United States Patent [19]

Brennen et al.

[11] Patent Number: 5,662,119
[45] Date of Patent: *Sep. 2, 1997

[54] STEERABLE STYLET AND MANIPULATIVE HANDLE ASSEMBLY

[75] Inventors: Kenneth R. Brennen, Fridley; Peter J. Pohndorf, Stillwater, both of Minn.

[73] Assignee: Medtronic Inc., Minneapolis, Minn.

[*] Notice: The term of this patent shall not extend beyond the expiration date of Pat. No. 5,396,902.

[21] Appl. No.: 426,355

[22] Filed: Apr. 21, 1995

Related U.S. Application Data

[63] Continuation of Ser. No. 13,126, Feb. 3, 1993, abandoned, which is a continuation of Ser. No. 751,278, Aug. 28, 1991, abandoned.

[51] Int. Cl.$^6$ .................................................... A61B 5/00
[52] U.S. Cl. ............................................................. 128/772
[58] Field of Search ............................... 128/772, 657, 128/656, 658; 604/95, 164, 170, 280, 281, 282, 283; 606/129

[56] References Cited

U.S. PATENT DOCUMENTS

| | | |
|---|---|---|
| 1,832,533 | 11/1931 | Creasy . |
| 2,118,631 | 5/1938 | Wappler . |
| 2,498,692 | 2/1950 | Mains ........................... 128/348 |
| 2,847,990 | 8/1958 | Ayre ................................. 128/2 |
| 3,416,531 | 12/1968 | Edwards . |
| 3,452,740 | 7/1969 | Muller .............................. 128/772 |
| 3,503,385 | 3/1970 | Stevens . |
| 3,521,620 | 7/1970 | Cook . |
| 3,528,406 | 9/1970 | Jeckel et al. . |
| 3,547,103 | 12/1970 | Cook . |
| 3,552,384 | 1/1971 | Tustin . |
| 3,605,725 | 9/1971 | Bentov . |
| 3,749,086 | 7/1973 | Kline et al. . |
| 3,789,841 | 2/1974 | Antoshkiw . |
| 3,841,308 | 10/1974 | Tate . |
| 4,136,703 | 1/1979 | Wittkampf . |
| 4,195,968 | 4/1980 | Emeny . |
| 4,215,703 | 8/1980 | Willson . |
| 4,245,624 | 1/1981 | Komiya ........................... 128/772 |
| 4,350,169 | 9/1982 | Dutcher et al. . |
| 4,357,947 | 11/1982 | Littleford . |
| 4,381,013 | 4/1983 | Dutcher . |
| 4,422,460 | 12/1983 | Pohndorf . |
| 4,506,680 | 3/1985 | Stokes . |

(List continued on next page.)

FOREIGN PATENT DOCUMENTS

| | | |
|---|---|---|
| 0274705 | 12/1987 | European Pat. Off. . |
| 2647005 | 5/1989 | France . |
| 3920707 | 6/1989 | Germany . |

*Primary Examiner*—Guy V. Tucker
*Attorney, Agent, or Firm*—Michael J. Juro; Harold Patton

[57] ABSTRACT

A steerable stylet and manipulative handle assembly especially adapted for guiding the introduction of an endocardial pacing or cardioversion/defibrillation lead or a catheter to a desired location in a patient's cardiovascular system. The steerable stylet or catheter designed to be introduced into the lumen of a lead comprises an outer, elongated tubular member of a length sufficient to extend through the length of the lead or catheter from its proximal opening to the distal end thereof, a traction element or pull wire extending generally through the length of the tubular member and within its lumen except for a predetermined distance in the distal portion thereof, and a manipulative handle coupled to the proximal ends of the tubular member and wire which may be employed with one hand to both rotate the tubular member and impart a continuously variable curve in the distal portion thereof. The distal portion of the tubular member is especially configured to be either attached to or cooperate with the distal end of the pull wire so that proximally-directed traction applied by the handle to the wire causes the distal portion of the tubular member to bend. The distal portion of the tubular member is provided with openings to allow the wire to exit and re-enter the lumen of the tubular member in the distal portion so that traction applied to the wire bows the tubular member into a curve of desired radius.

8 Claims, 7 Drawing Sheets

U.S. PATENT DOCUMENTS

| | | |
|---|---|---|
| 4,577,642 | 3/1986 | Stokes . |
| 4,606,118 | 8/1986 | Cannon et al. . |
| 4,624,266 | 11/1986 | Kane . |
| 4,677,990 | 7/1987 | Neubauer . |
| 4,733,669 | 3/1988 | Segal ........................................ 128/663 |
| 4,799,496 | 1/1989 | Hargreaves et al. .................... 128/772 |
| 4,807,626 | 2/1989 | McGirr .................................... 128/772 |
| 4,813,434 | 3/1989 | Buchbinder et al. . |
| 4,815,478 | 3/1989 | Buchbinder et al. .................... 128/772 |
| 4,824,435 | 4/1989 | Giesy et al. ............................... 604/49 |
| 4,846,175 | 7/1989 | Frimberger . |
| 4,886,067 | 12/1989 | Palermo .................................. 128/657 |
| 4,921,482 | 5/1990 | Hammerslag et al. ................... 604/95 |
| 4,976,691 | 12/1990 | Sahota ...................................... 604/96 |
| 5,277,189 | 1/1994 | Jacobs . |
| 5,396,902 | 3/1995 | Brennan et al. ......................... 128/772 |

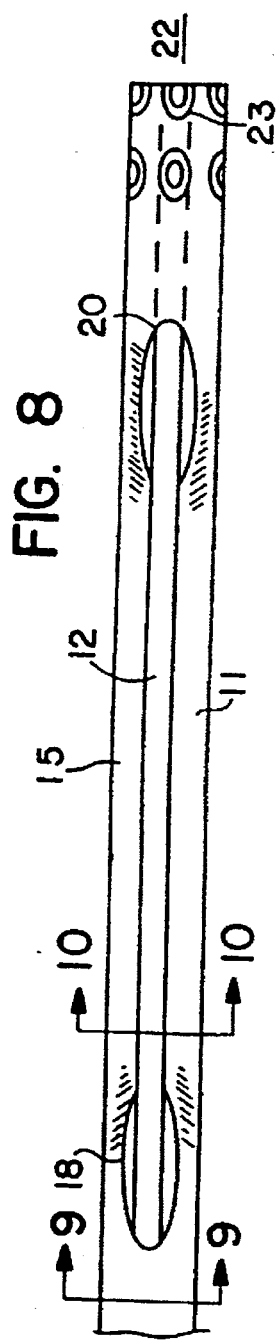
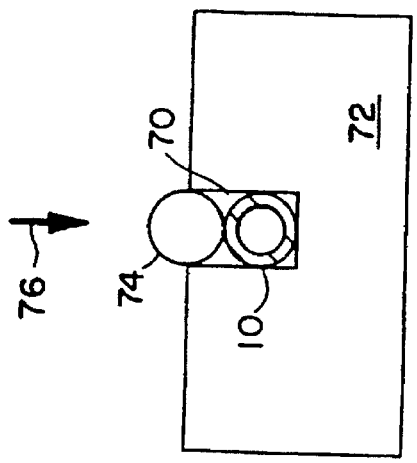
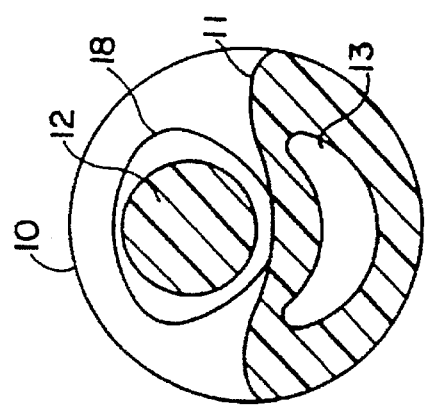
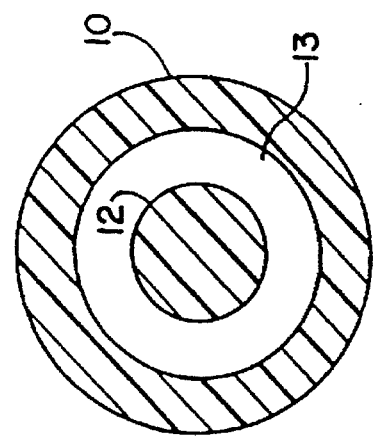
FIG. 8
FIG. 9
FIG. 10
FIG. 11

STEERABLE STYLET AND MANIPULATIVE HANDLE ASSEMBLY

This is a continuation of application Ser. No. 08/013,126 filed on Feb. 3, 1993, now abandoned which is a continuation of Ser. No. 07/751,278, filed on Aug. 28 1991 now abandoned.

BACKGROUND OF THE INVENTION

1. Field of the Invention

The present invention relates to a wire guide or stylet assembly for the introduction of medical catheters or electrical leads to a desired site within the patient's body, and specifically to a steerable stylet assembly for imparting a desired dynamic curvature in the distal portion of a catheter or lead during its introduction in order to guide it through curvature in the patient's vascular system and to a desired site in the patient's cardiovascular system.

2. Description of the Prior Art

The marked advances in cardiac and vascular surgery in the past few years and other medical problems that require diagnostic study of the vascular beds and systems as well as the advances in pacing and cardio version, has led to the extensive use of cardiac or vascular catheters, such as percutaneous transluminal coronary angioplasty (PTCA) catheters and transvenous or endocardial pacing and cardioversion leads. The insertion of a relatively long catheter or lead body to an internal site requires advancement of the catheter or lead into branch vessels at varying angles relative to the feeding direction of the catheter or a lead.

In respect to the introduction of PTCA catheters, for example, several techniques for introducing such catheters are available, including the cut-down method and the Seldinger techniques. The Seldinger technique involves surgically opening a vein or artery with a needle, inserting a guide wire into the vein or artery through the lumen of the needle, withdrawing the needle, inserting over the guide wire a dilator located inside an associated hemostasis valve and sheath, removing the dilator and inserting a catheter through the hemostasis value and sheath into the blood vessel. In this procedure, flexible spring wire guides of type disclosed in commonly assigned U.S. Pat. No. 4,815,478 to Buchbinder, et al, and the numerous patents referenced therein are steered to the desired internal site by remotely deflecting the tip of the guide to facilitate movement of the guide wire around or through a curved path in the vessel. The steerable spring guide wire of the 478 patent possesses a flexible tip constructed with flexible spring coil wire extending from the elongated guide wire body and coupled to a long tip which is additionally coupled to a deflection wire extending through the flexible tubing body and the spring coil as well as a control wire extending through the lumen provide for the deflection of the distal tip portion by the application of traction to the proximal end of the control wire. The control wire remains within the confines of the elongated tubular body as well as the loosely-wound flexible spring coil distal portion thereof. As stated above, once the distal portion of the guide wire is advanced to the desired internal site, then the lumen of the tubular catheter is advanced over the guide wire until its distal tip is advanced to the desired internal site, whereupon the guide wire is withdrawn.

In the pacing and cardioversion context, it is well known to guide the insertion and proper placement of an endocardial lead to a desired internal site in a chamber of the patient's heart or in a vessel, such as the coronary sinus, through the use of a stiffening stylet inserted into the lumen of the pacing or cardioversion lead. Generally speaking, it is highly desirable that pacing and cardioversion leads be so flexible through their length that they are capable of flexing with the movement of the heart and other muscular movement so as to void the fracture of the lead body due to its cumulative stressing. Thus, pacing and cardioversion leads are generally too limp to be advanced on their own through the venus system to the desired internal site and it has been commonplace for many years to employ thin wire stylets extended down the lumen of the lead to stiffen the entire assembly and to impart a desired degree of curvature of the tip of the lead body during insertion. To accomplish this desirable result, the solid inner stylet wire is given a temporary bend or curvature near its distal end when it is outside the lumen by the physician. After insertion through he lumen, the curved distal portion facilitates movement of the distal tip of the lead into branch vessels at certain points as the lead is advanced and thereafter assists in directing the lead tip to the desired internal site within the patient's heart or cardiovascular system.

It is also commonly known to employ a stylet to straighten an atrial pacing lead, which is provided with a permanent "J"-shaped bend to facilitate both the positioning and the retention of the atrial electrode in the patient's atrial appendage as taught, for example, in U.S. Pat. No. 4,136,703, issued to Wittkampf. Insertion of these "J"-shaped leads is greatly facilitated through the use of a straight solid inner stylet which, in this case, straightens the bend normally fixed within the distal end of the lead itself.

Such endocardial pacing and cardioversion leads typically comprise a length of coiled wire conductor formed around an axial lumen and encased within a suitable insulating material, such as silicone rubber or polyurethane, that is substantially inert to body fluids and tissues. A hollow connector pin is attached coaxially to the lumen and electrically to the proximal end of the conductor. An electrically conductive electrode at the distal end of the conductor is adapted to be placed in contact with the endocardium or within the coronary sinus of the patient. When more than one length of separately-insulated coiled wire conductors is employed in modern pacing and cardioversion leads, each coiled wire conductor is wound coaxially around the centrally-disposed lumen which extends through the connector pin and the corresponding lengths of coiled wire conductors to the distal end of the lead body. The lumen receives the stiffening stylet of cylindrical wire for imparting stiffness and curvature to the distal portion of the lead body to facilitate its advancement through the venus system and to the desired internal site. Further details of the construction and utility of such endocardial pacing leads may be obtained and referenced to U.S. Pat. Nos. 4,506,680, 4,577,642, 4,606,118, and 4,711,281, all incorporated herein by reference.

Insertion of such endocardial pacing and cardioversion leads frequently requires that the physician commence the introduction through a lead introducer introduced into a vein through a skin puncture made at a small angle to the vein. At the outset, the stylet may be left straight or provided with a certain degree of curvature to facilitate the introduction into the vein and through the initial curvature thereof. Thereafter, and from time to time, as the physician directs the distal tip of the lead in a tortuous path leading to the right heart, it may be necessary to withdraw the stylet and either substitute a new stylet or impart a different curvature to the distal portion of the stylet, reinsert it and advance the distal portion of the lead a bit further until another obstacle to advancement is encountered. It is undesirable to contaminate the lumen with blood during this process because drying blood can form a strong adhesive bond between the stylet and the pacing lead, making stylet removal impossible and rendering the lead unusable. Moreover, the continual withdrawal and reintroduction of stylets is time consuming and offers the potential of damaging the lead in the process.

In order to avoid the withdrawal and reintroduction of stylets, various approaches have been proposed including those disclosed in commonly assigned U.S. Pat. No. 4,381,013 to Dutcher and U.S. Pat. No. 4,677,990 to Neubauer. The '013 patent is directed to the use of a two-piece stylet having an inner solid portion for enabling a shape to be imparted to the lead to facilitate introduction in the fashion as described above and an outer tubular portion which enables the transmission of torque applied by the implanting physician at the proximal end to be transmitted to a helical fixation means located at the distal end of the lead. The transmission of this torque allows the helical fixation means to be screwed into the endocardial tissue. Thus the solid wire inner stylet operates in the same fashion as the conventional solid wire stylets described above.

The '990 patent discloses the combination of a removable stylet stiffening wire and one or more threads having very low elasticity which are coupled near the distal end of the lead or at selective locations along the lead body extending for a portion of the length of the lead within the lead lumen and for a further portion outside the lumen but within the sheath. With the stylet inserted, traction applied to the proximal portion of the thread or threads imparts a curvature into the lead body as the thread is pulled taut. The curvature is dictated by the locations at which the thread or threads are directed in the space between the outer insulation sheath and the coiled wire conductor. To achieve easier bending, the stylet is described as having portions of reduced thickness along its length in parallel with the location of the threads passage outside the lumen.

The '990 patent addresses concerns raised by the conventional technique of withdrawing, imparting a new curve, and reinserting the stiffening stylet during the implantation procedure.

The use of the separate thread and stylet in the '990 patent and the two-piece stylet of the '013 patent as well as the conventional one-piece stylets usually require the physician to employ both hands in manipulating the lead and stylet to advance and withdraw the stylet and rotate the lead body in manipulating the advancement of the distal portion of the lead through the venus system or into particular desired sites for lodging the electrodes. U.S. Pat. No. 3,452,740 to Mueller discloses a spring guide manipulator for imparting a curvature and rotation in a spring guide by one-handed use of a manipulative handle. The spring guide wire includes the conventional inner straight wire coupled to the distal end of the coiled wire of the distal portion of the spring wire guide. When the handle is attached to a guide wire and a catheter is fitted over the guide wire, it is reported that the handle may be employed to both rotate the guide wire and catheter as well as place a curve in the distal portion of the catheter.

Despite these advances in the guide wire and catheter prior art as well as the pacing and cardioversion lead stylet prior art, a need remains for a simple, easy-to-use stylet or catheter guide wire assembly which provides a wide degree of dynamic curvature to the lead or catheter being advanced by the physician.

SUMMARY OF THE INVENTION

It is therefore an object of the present invention to provide a simple and easy-to-use stylet and manipulative handle assembly for imparting a dynamic curvature to the distal portion of a catheter or lead during its advancement through a blood vessel.

It is a further object of the present invention to make such stylet and manipulative handle assembly easy-to-use with one hand.

It is a still further object of the present invention to provide such a stylet and handle assembly of the character stated which is simple in design, rugged in construction and economical to manufacture.

These and other objects of the present invention are realized in a stylet for the advancement of a catheter or a lead having a lumen extending therein between a proximal and distal thereof, wherein the stylet comprises an elongated tubular member having a proximal and a distal end, with at least one aperture located a predetermined distance from the distal end of said tubular member, a traction element or pull wire attached at the distal end of said tubular member and extending loosely outside said lumen for said predetermined distance, through said aperture and said lumen, and from the proximal end of the tubular member; and a manipulative handle coupled to the proximal end of said tubular member, the manipulative handle compromising body member attached to said proximal end of said tubular member and receiving said proximal end of said wire therewithin, a slide member adapted to slide along said body member through manipulation thereof by the physician and a control lever pivotally attached to said body member, fixedly attached to said pull wire and loosely coupled to said sliding member.

In the preferred embodiments thereof, the tubular member preferably possesses a second aperture more distally located then the first aperture, and the pull wire extends from the distal end of the tubular member through the lumen, out the second aperture, alongside the outer surface of the tubular member and back within the lumen through the first aperture so that when traction is applied to the pull wire, it tends to cause the tubular member along the predetermined distance to bow outward and away from the taut pull wire lying outside the lumen. The pull wire may be fixedly attached to the distal tip of the tubular wire or it may be coupled to an enlarged member that is too large to pass through the lumen of the tube and bears against the distal end when traction is applied, but otherwise may allow the advancement of the distal end of the pull wire beyond the distal end of the tubular member.

In further preferred embodiments of the present invention, the predetermined distance along the tubular member may comprise either a cut-out section or a flattened section of the tubular member between the first and second apertures therein.

In accordance with the practice of the present invention, the distal portion and length of the tubular member and pull wire stylet may be introduced into the lumen of a lead or catheter and the proximal end thereof may be coupled to the housing of the handle assembly. Manipulation of the distal portion of the lead or catheter may be accomplished by rotating the handle while advancing or retracting the slide member, thereby releasing or applying traction to the pull wire and straightening or curving the distal portion of the catheter or lead.

Advantageously, as traction is applied continuously the lever provides a mechanical advantage of 2:1 or more between the force needed to pull the wire directly and the force needed to operate the slide. This reduces the mechanical force to be applied by the fingers and also allows the slide member to be temporarily fixed in one location with the application of an external force. A continuous, dynamic range of curvature from zero to one hundred eighty degrees may be induced in the distal portion of the lead or catheter. Lateral displacement of the pull wire outside the lumen of the tubular member is restrained by the lumen of the catheter or lead. Thus a very small movement of the slider in relation to the body of the manipulative handle causes a large change in curvature of the distal portion of the lead or catheter. The 2:1 mechanical advantage of the lever expands this range of control motion of the slide member and allows for increased fineness of control of the stylet curvature.

BRIEF DESCRIPTION OF THE DRAWINGS

These and other objects, advantages and features of the invention will become more apparent and the invention will be more fully understood by reference to the drawings of the preferred embodiments thereof, wherein:

FIG. 8 is a top view of the first embodiment of the distal portion of the style of the present invention;

FIG. 9 is a cross-sectional view of the elongated tubular member and pull wire along lines A—A of FIG. 8;

FIG. 10 is a cross-sectional view of the elongated tubular member and wire taken along lines B—B of FIG. 8;

FIG. 11 is a cross-sectional view of a die and tool for flattening the predetermined length of the distal portion of the tubular member depicted in FIG. 8;

DESCRIPTION OF THE PREFERRED EMBODIMENTS

As described above, the steerable stylet and manipulative handle assembly of the present invention may be advantageously employed in either the introduction of a hollow tubular catheter, a sensor-bearing hollow tubular catheter or an intravascular electrical sensing and/or stimulation lead, such as a transvenous or endocardial pacing or cardioversion lead. The specific catheters or leads are not illustrated or described except in reference to their cooperation with the stylet and manipulative handle of the present invention.

Figure 1:
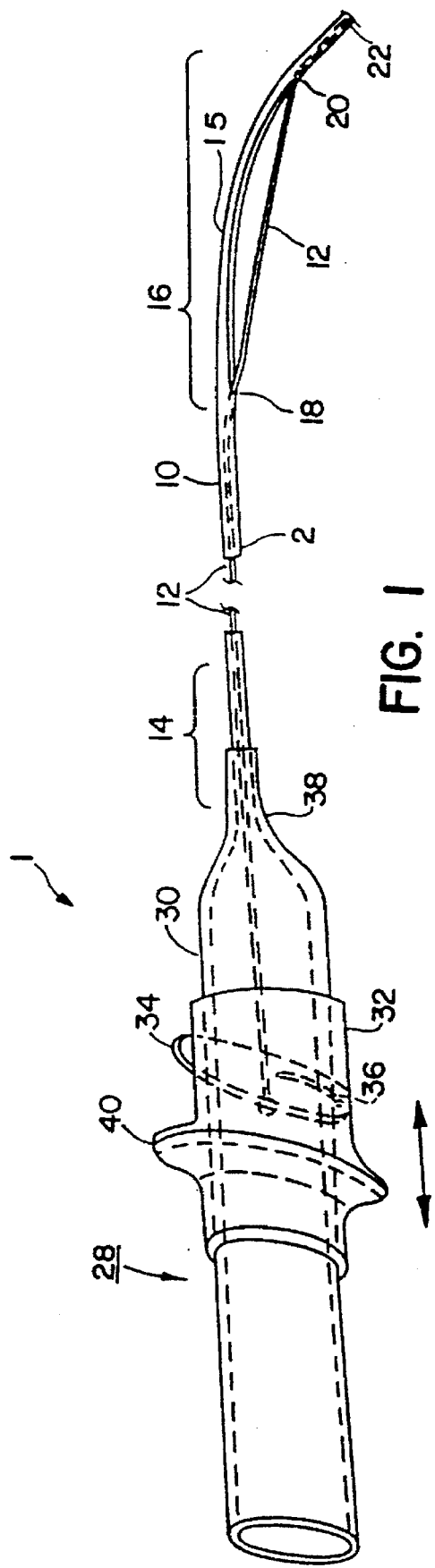
FIG. 1 is a perspective view illustrating the steerable stylet and manipulative handle assembly of the present invention.

Turning now to FIG. 1, it illustrates a perspective view of the stylet and manipulative handle assembly of the present invention assembled together and illustrating a certain degree of curvature imparted in the distal end thereof through retraction of the pull wire in relation to the elongated tubular member.

The steerable stylet assembly illustrated in FIG. 1 comprises the elongated tubular member 10 and pull wire 12 having a proximal section 14 and a distal section 16 with an elongated intermediate section extending therebetween (not specifically illustrated). The distal portion 16 possesses first and second apertures 18 and 20 separated apart a predetermined distance. As described hereafter, the predetermined distance including the distal straight section extending between the second opening 20 and the distal tip 22 is preferably in the range of 2.5 to 4.0 inches. The radius of curvature to be imparted as the pull wire 12 is retracted proximally is preferably between 0.50 and 1.5 inches although other dimensions can also be used. In FIG. 1 a much greater radius of curvature is illustrated as very little traction is exerted on pull wire 12.

As depicted hereafter in conjunction with FIG. 8, the pull wire 12 mechanically cooperates with the distal tip 22 of the tubular member 10 and extends within the lumen 13 of the tubular member 10, out the second opening 20 and alongside the tubular member 10 the predetermined distance, whereupon it extends through the first opening 18 and proximally through the lumen 13 of the tubular member 10 to the proximal end 14. The pull wire 12 is only fixedly attached to the tubular member 10 at the distal end 22, and, in certain embodiments, it may extend distally from the distal end 22 and terminate in an enlarged element having a diameter greater than the inside diameter of the lumen 13.

Turning now to the manipulative handle of the stylet assembly, it includes the housing 30, the slidable member 32, the lever 34 and a spring wire clip element 36 which are attached to the proximal portion 14 of the steerable stylet. In this regard, the tubular member 10 is mechanically attached to the opening in the neck-down portion 38 of the cylindrical housing 30 and terminates therewithin. The pull wire 10 extends within the housing 30 to be coupled mechanically to the lever 34 as illustrated more completely in FIGS. 2 and 3.

In use, the stylet tubular member 10 and pull wire 12 are inserted into the connector pin opening of a lead which is axially arranged with the lumen within the lead body itself in the well-known fashion or into the lumen of a catheter. A press fit of the neck-down portion 38 with the lead connector pin opening or the catheter lumen opening is relied upon to hold the lead or catheter in fixed relation with the housing 30. After this mechanical connection is effected, the lead or catheter may be rotated by rotation of the housing 30, and curvature may be imparted by the thumb engageable, slideable member 32 acting on the lever 34 and pull wire 10. The overall dimensions of the housing 30 and slide member 32 are configured to fit within the physician's hand so as to allow thumb engagement with the circular ridge 40 to move the slideable member 32 back and forth on housing 30 to increase or decrease the radius of curvature in the distal portion 16 of the stylet assembly. Friction between the outer surface of the housing 30 and the inner surface of slide member 32 is relied on to hold lever 34 in a desired position.

Figure 2:
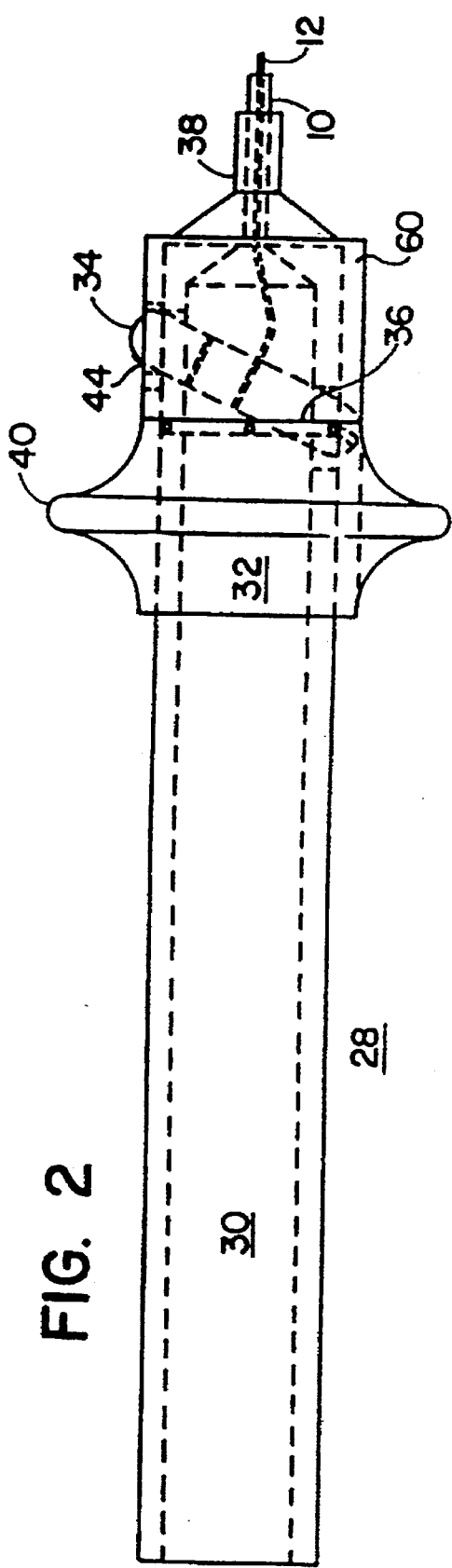
FIG. 2 is a side elevation view of the manipulative handle of the present invention depicting the slide member advanced distally thus straightening the distal portion of the steerable stylet.
Figure 3:
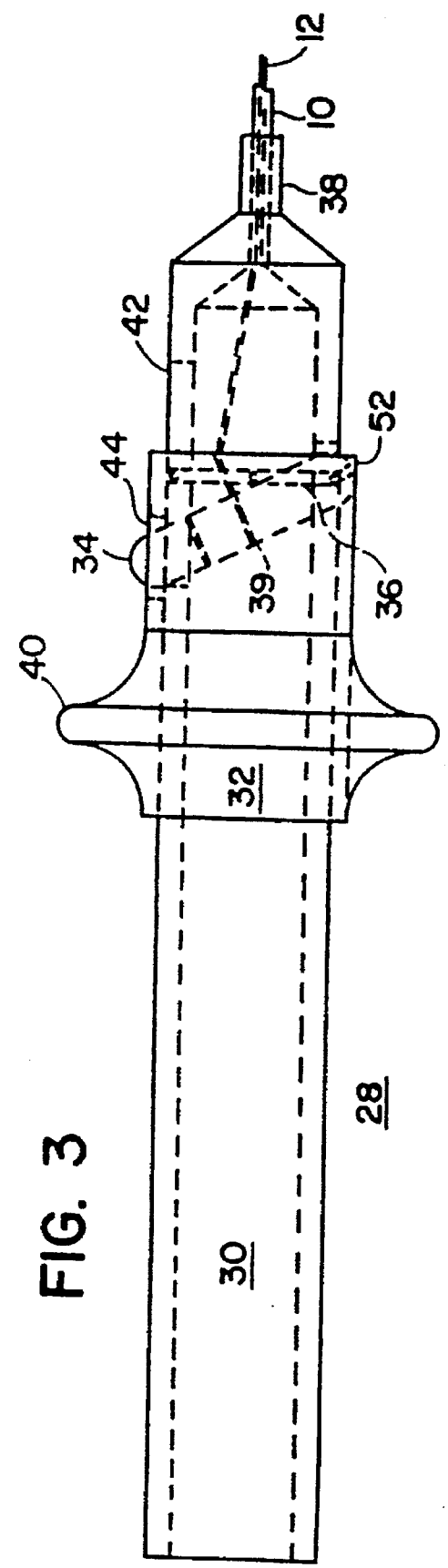
FIG. 3 is a side elevation view of the manipulative handle of the present invention with the slide member retracted proximally to apply traction to the pull wire and impart curvature to the distal portion of the stylet.

Turning now to FIGS. 2 and 3, side elevation, phantom line, views of the manipulative handle 28 in the relaxed and fully tractioned positions of the slideable member 32 and lever 34 in relation to housing 30 and certain internal broken line components thereof are illustrated, respectively. Essentially, the lever 34 (depicted in FIG. 6) is pivoted at its fixed end 35 on wire clip 36, and its free end 37, captured by slot 44 in the top surface of slideable member 32, is pivoted back and forth by movement within an elongated channel 42 in housing 38. The proximal end of pull wire 12 is fitted in an opening 39 along the body of the lever 34 so that it is pulled back and forth with movement of the slide element 32.

Figure 4:
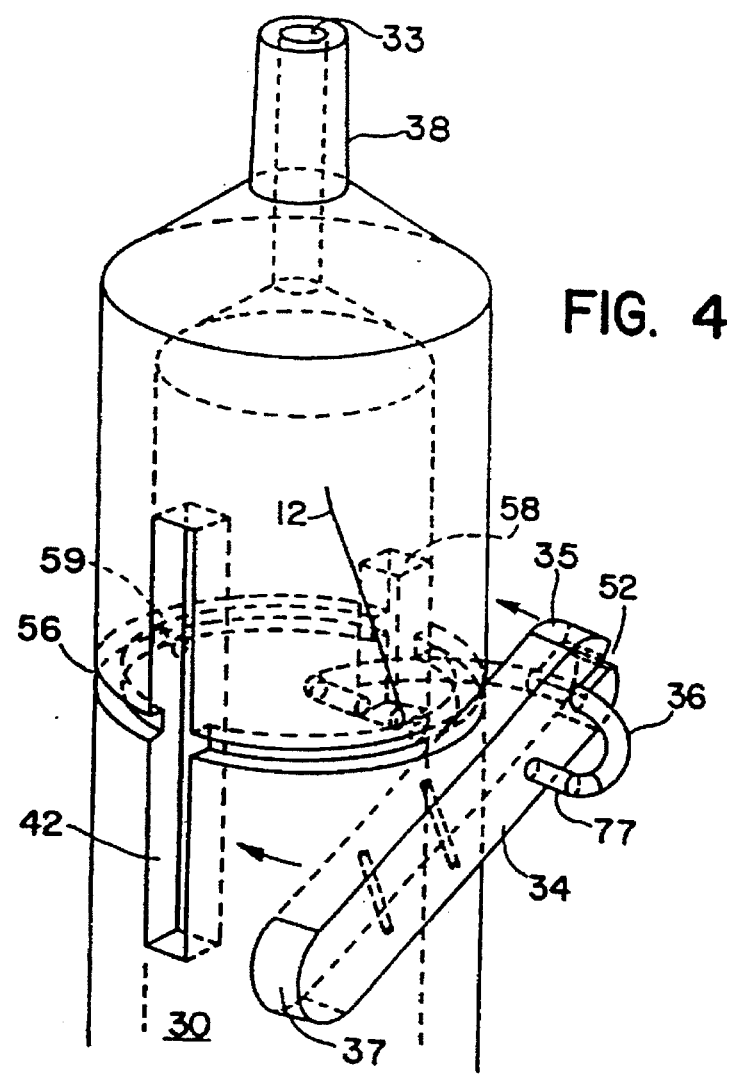
FIG. 4 is a perspective view of the housing of the manipulative handle showing its internal and external configuration.
Figure 5:
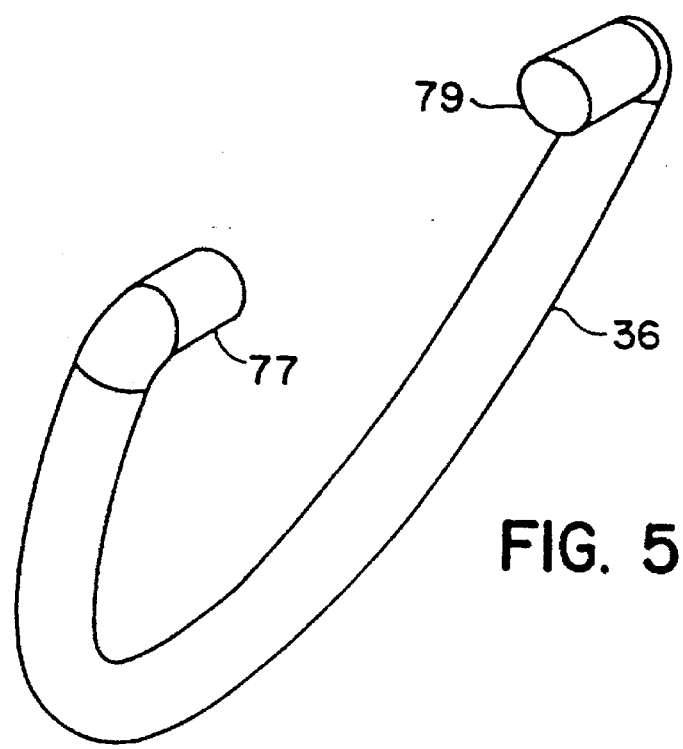
FIG. 5 is a perspective view of a spring clip inserted in a groove in he housing of the manipulative handle.
Figure 6:
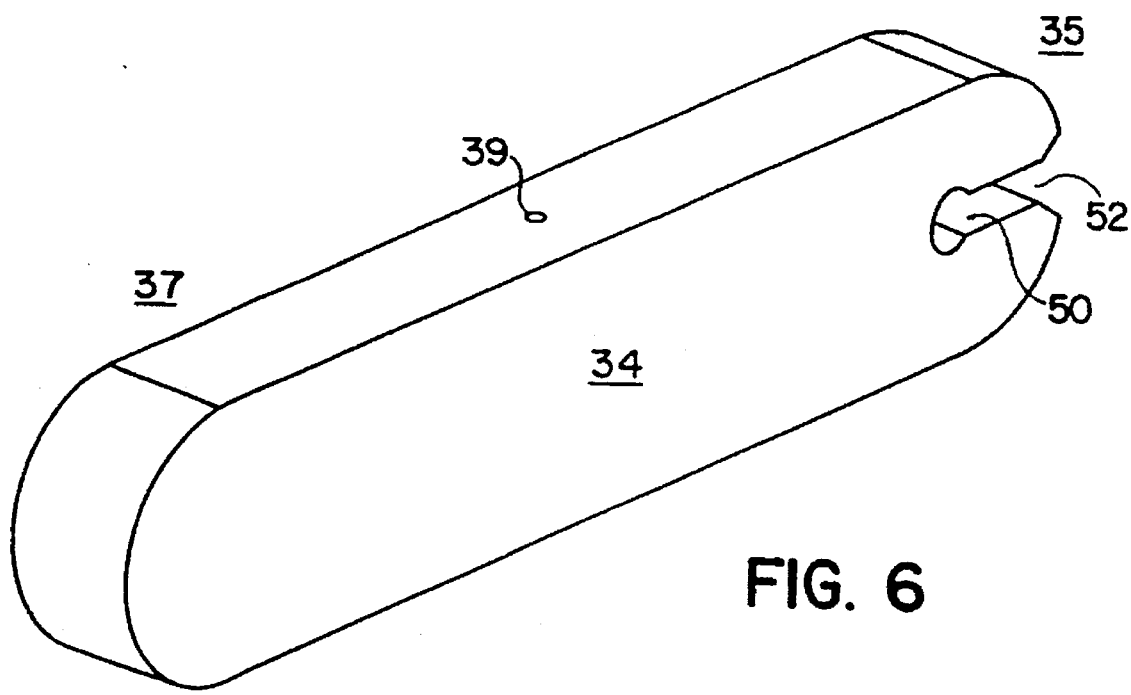
FIG. 6 is a perspective view of the lever used in the housing of the manipulative handle.

Turning now to FIG. 4, a perspective view of the housing 30 illustrates the manner in which the lever 34 and the clip 36 are interconnected with the proximal end of the pull wire. The lever 34, shown in FIG. 6, is a flat-sided elongated member have a pair of semicircular shaped ends 35 and 33. A clothespin shaped hole 50 and slit 52 in the fixed end 35 thereof are adapted to be slipped over the wire clip 36. The wire clip 36, shown in FIG. 5, is generally C-shaped and adapted to fit within and wrap about the circumference of the groove 56 extending across the bottom opening 58 illustrated in FIG. 4. The bottom opening 58 receives the end of the lever 34 which snaps onto the C-shaped ring 36 by action of the groove 52. The shape and springiness of the C-shaped clip 56 retains it in position once the clip's free ends 37, 39 are snapped into the groove 56 and holes 59 in groove 56 on each side of housing 30. Similarly, the lever 34 is snapped into place so that hole 50 fits around the exposed portion of the wire clip 36 traversing the bottom opening 58 of housing 30.

The top opening 42 in housing 30 extends a distance sufficient to provide the desired degree of movement of the lever 34 and pull wire 12 with regard to the tubular member 10.

Figure 7:
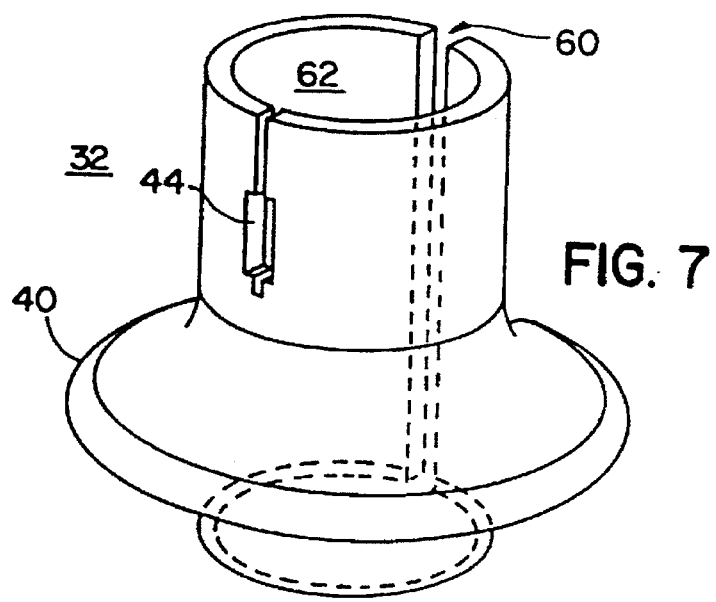
FIG. 7 is a perspective view of the slide member of the manipulative handle.

Referring now to FIG. 7, perspective view of the slideable member 32 illustrates the opening 44 for receiving the free end 37 of the lever 34 and moving it back and forth within the opening 42 of the housing 30 as well as an opening 60 within which the other end of the lever 34 is accommodated in the assembly depicted in FIGS. 2 and 3.

Preferably, the inside diameter 62 of the slideable member 32 is undersized somewhat with respect to the outside diameter of the housing 30 so that friction may be relied upon to hold the slideable member in any position depicted in FIGS. 1 to 3 while the lead and stylet assembly is advanced, withdrawn or rotated by the physician in manipulating the position of the distal end of the catheter or lead.

Turning now to FIGS. 8 to 13, first and second preferred embodiments of the distal portion 16 of the stylet assembly depicted in FIG. 1 are illustrated. In these embodiments, it is anticipated that tubular member 10 is constructed of hypodermic needle tubing, such as 304W stainless steel tubing having an outside diameter in the range of 0.012 to 0.016 inches with about 0.0035 inch wall thicknesses. The pull wire is preferably 0.005–0.007 inch stainless steel wire of high tensile strength.

The first preferred embodiment of forming the first and second openings 18 and 20 and the treatment of the predetermined length of tubular member 10 extending therebetween is illustrated in FIGS. 8 to 11. In this embodiment, the predetermined length of the tubular member 10 is flattened between the openings 18 and 20 to provide a predetermined bias to curve away from the length of wire 12 as it is drawn taut between the openings 18 and 20. The flattening also renders the tubing in the flattened section more resistant to kinking and better able to flex to virtually a full 180 degrees.

The distal portion 16 illustrated in FIG. 8 includes the first and second openings 18 and 20, the distal tip 22 and the length of wire 12 extending from its point of attachment 23 made in the distal tip 22 out the second opening 20, alongside the flattened predetermine length 11 and back into the lumen 13 through the first opening 18.

Turning now to FIGS. 9 and 10, they illustrate cross sectional views of the tubular member 10 and pull wire 12 taken along section lines A—A and B—B, respectively. In FIG. 9, the pull wire 12 is shown residing within the lumen 13 of the tubular member 10. In FIG. 11, the wire 12 is depicted extending from the opening 18 in the tubular member 10 and distally along the flattened surface 11 of the tubular member 10 at the point where the section B—B was taken in FIG. 8. The original lumen 13 in that section is compressed substantially.

Turning now to FIG. 11, it depicts a simple die for flattening section 11 of the distal portion 16 by placing that portion of the tube 10 in a groove 70 in the elongated block 72, fitting an elongated hardened steel pin 74 on top of the tubular member 10 within groove 70 and applying force in the direction of the arrow 76 to flatten the tubular member. Preferably the width of the groove 70 is selected to be slightly larger than the outside diameter of the tubular member 10.

This section of this steerable stylet that actually produces the dynamic curvature is strengthened and stiffened by flattening the tube rather than removing metal or cutting an elongated window. The alternative manner in which an elongated opening may be obtained and an alternative manner of coupling the distal end of the tubular member 10 and the pull wire 12 are depicted in FIGS. 12 and 13.

Figure 12:
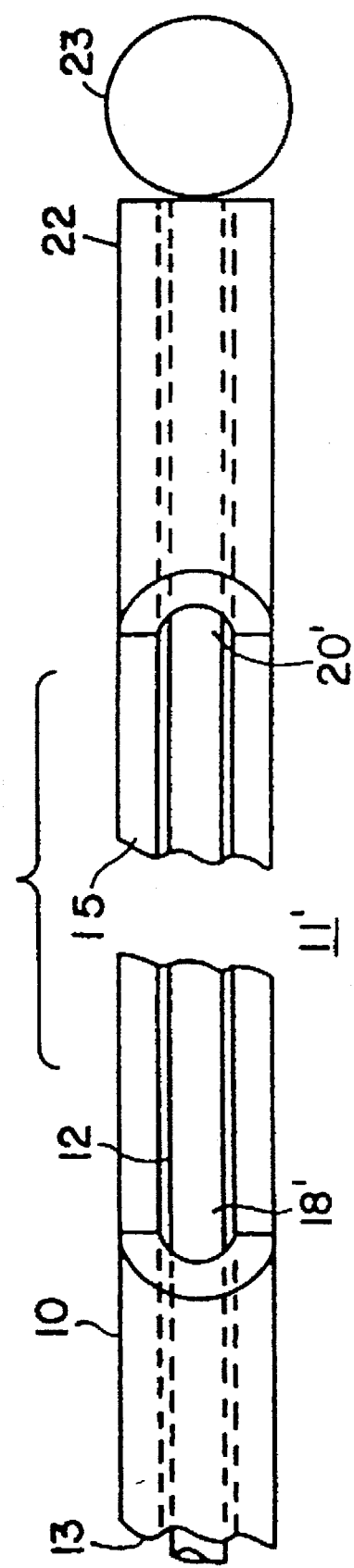
FIG. 12 is a top view of a distal portion of a further embodiment of the steerable stylet of the present invention.
Figure 13:
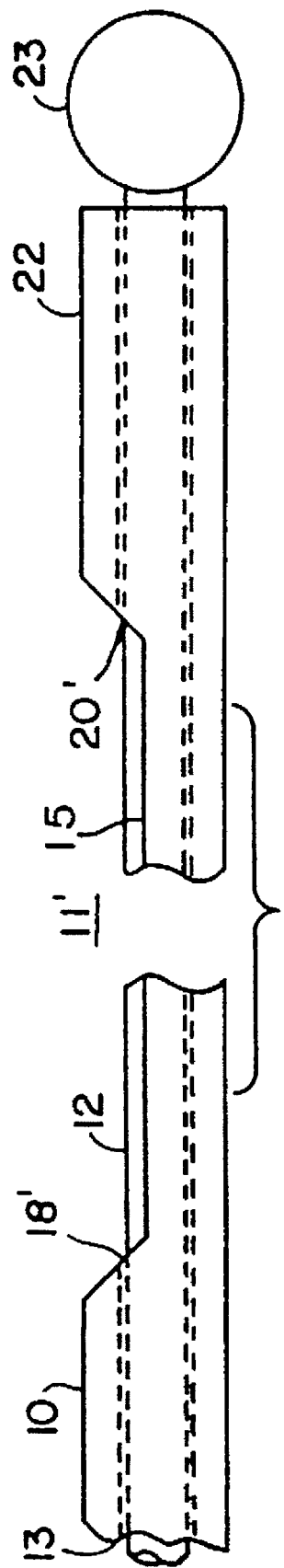
FIG. 13 is a side view of the cut-out section of FIG. 12.

FIGS. 12 and 13 are top and side views of the distal portion 16 of the steerable stylet assembly wherein the two openings 18 to 20 and the flattened section 11 are replaced by an elongated cutaway portion of the tube 10. The elongated cutaway portion depicted in FIGS. 12 and 13 is illustrated in the same fashion as FIGS. 8 to 11 in that the first and second openings 18 and 20 are replaced by first and second cuts 18' and 20' and the elongated flattened portion 11 is replaced by the cutaway portion 11'.

There is no fixed attachment of the pull wire to the distal end 22 of the tubular member 10 depicted in FIGS. 12 and 13. Instead, the pull wire 10 is adapted to terminate in ball shaped element 23 having a diameter greater than the inside diameter of the lumen 13. This construction allows the same traction forces to be applied as in the fixed end embodiment illustrated in FIGS. 8 to 10. It also allows for the advantageous use of a rounded end or ball-tip stylet which may reduce perforations of the lumen of the lead body or the thin wall catheter that may be employed with the stylet assembly. Alternative tip designs may be provided to act as keys to engage with active fixation elements which may be rotated out of or extended from the distal end of an active fixation pacing lead in the manner described in the above referenced '013 patent, for example.

In constructing prototypes of the steerable stylet of the present invention, it was found that the cutaway tubing embodiment of FIGS. 12 and 13 was inferior to the flattened embodiment of FIGS. 8 to 11 in resistance to kinking. It has also been found that the flattened embodiment is easier to manufacture than the cutaway embodiment. In the course of experimentation, an attempt was also made to fabricate a steerable stylet merely having the first and second spaced apart openings 18 and 20 in the tubular lead body without either cutting away a portion of the body or deforming that portion between the two openings. Experiments conducted with the pull wire extending outside the tube between the first and second openings and fixedly attached at the distal end thereof showed an unacceptable tendency of the tube to kink at even moderate curvatures. Consequently, there is presently a belief that the embodiment of FIGS. 8 to 11 with either the distal end of the pull wire 10 crimped to or engaged with the distal end 22 of the tubular member 10 is preferred to the embodiment of FIGS. 12 and 13 or the unmodified tubular embodiment.

Figure 14:
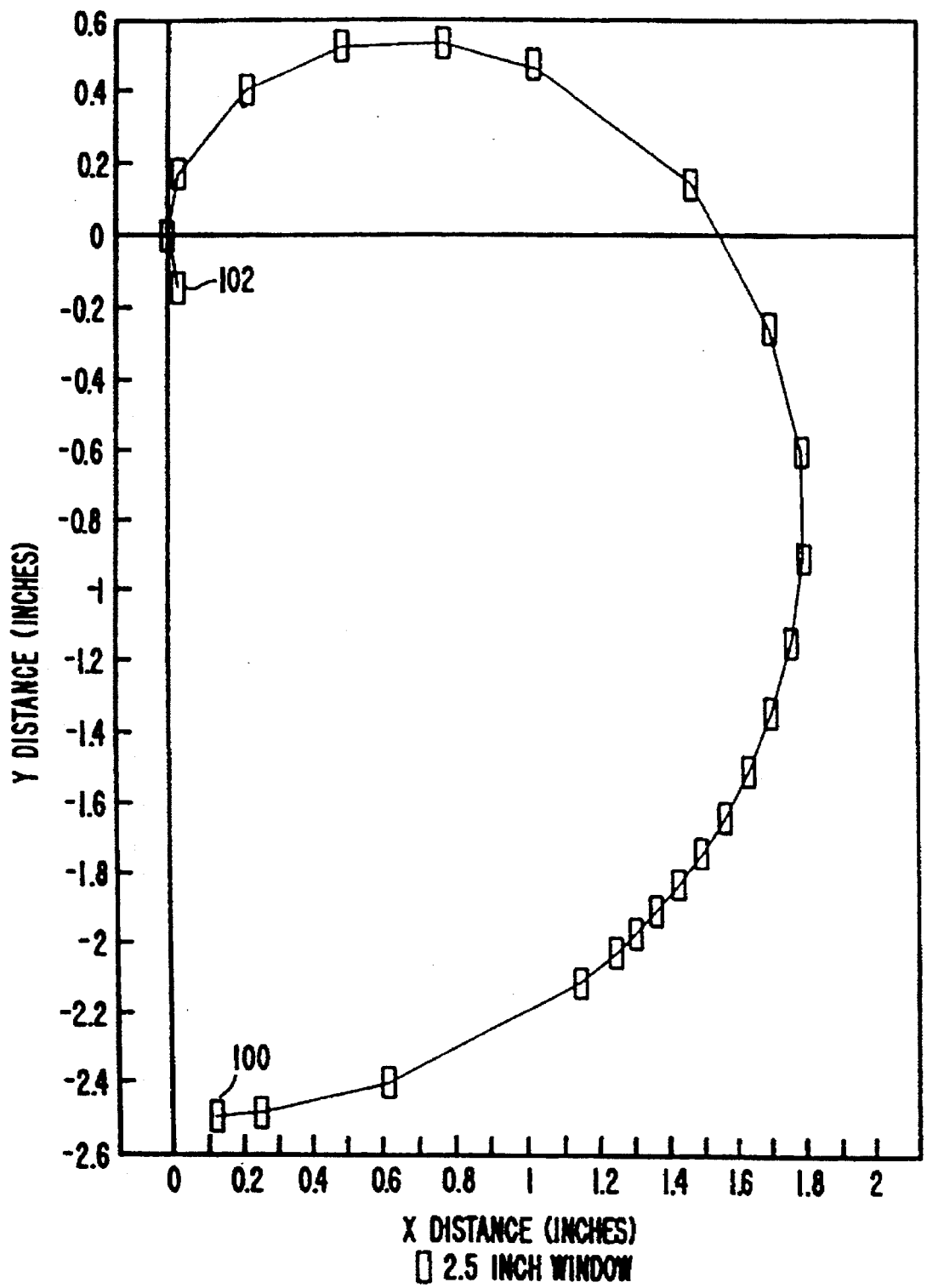
FIG. 14 is an illustration of the dynamic curvature in the X-Y plane imparted by a prototype steerable stylet and manipulative handle assembly in accordance with the teachings of the present invention.

Turning now to FIG. 14, it is an illustration of the dynamic curvature in the X-Y plane imparted by a prototype steerable stylet and manipulative handle assembly in accordance with the teachings of the present invention. In FIG. 14, the origin of coordinates is the beginning of the deflectable part of the stylet tubular member 10, and the illustrated points (shown by the rectangles) represent the coordinates of the tip 22 at various states of deflection for a stylet with a predetermined distance of 2.5 inches for the extra-lumenal wire 12. The curve represents the locus of all points through which the tip will pass as the stylet is dynamically deflected and illustrates that the stylet tip 22 may be deflected from straight at point 100 to point 102 where it forms a complete circular loop.

The steerable stylet and manipulative handle assembly described above in conjunction with its preferred embodiment provides the desirable features of stiffness, torque transmission, and dynamic curvature for the range of curvatures desired in use as illustrated in FIG. 14 with reasonable force and high resistance to kinks. In any given implant procedure, the ability to provide dynamic curvature changes avoids withdrawing the stylet to change its curvature as the lead is passed. The one-handed manipulation of the handle facilitates the achievement of dynamic curvature while advancing and rotating the lead or catheter. In animal tests, it was found that the dynamic curvature facilitated the locating and passage of the distal portion of a pacing lead into the coronary sinus with unaccustomed ease.

The embodiments as described include only a single flattened or cutaway portion of the tubular member 10 and the pull wire 12 extending the predetermined distance extra-lumenally thereby. It will be understood that in certain applications, it may be desirable to provide for a further or a series of further replications thereof along the length of the stylet.

As many apparently widely different embodiments of the present invention can be made without departing from the spirit and scope thereof, it is to be understood that the invention is not limited to the specific embodiments thereof except as defined in the appended claims.

What is claimed is:

1. A stylet and manipulative handle assembly controllable to form selected curvatures in a distal portion of a catheter or lead having a lumen extending therethrough comprising:

flexible, elongated tubular member having proximal and distal ends and proximal and distal portions thereof and having an internal axially disposed lumen;

at least one traction element extending through said lumen and attached to said distal end portion of said tubular member, at least a portion of said traction element eccentrically guided outside and parallel to said tubular member for a distance along said tubular member, said traction element having a proximal end projecting from an opening in said proximal portion of said tubular member; and manipulative handle means attached to said proximal portion of said tubular member and to the proximal end of said traction element for exerting tension on said traction element to form the said tubular element to a desired degree of curvature depending upon the amount of tension and whereby said catheter or lead is similarly curved; and wherein said manipulative handle comprises:
a longitudinal housing having a distal end thereof attached to said proximal end of said tubular element and receiving said proximal end of said traction element therewithin;

a reciprocating hinge lever coupled for pivotal motion with respect to said longitudinal housing and adapted to be disposed transversely therewithin;

means for attaching said proximal end of said traction element to said lever; and slide means coupled to said lever and adapted to slide upon said longitudinal housing for advancing and retracting a free end of said lever and thereby releasing and applying traction to said traction element to release or induce curvature in the distal portion of said elongated flexible tubular member.

2. The assembly of claim 1 wherein said elongated tubular member has a selected profile coextensive with said distance along said tubular member for decreasing the tendency of the tubular member to kink when curved out by the application of traction to said traction element.

3. The assembly of claim 2 wherein said profile is a region of reduced cross section effected by compressing said tubular element upon itself.

4. The assembly of claim 2 wherein said profile is effected by cutting away one side of said tubular member.

5. A stylet and manipulative handle assembly controllable to form selected curvatures in the distal portion of a catheter or lead having a lumen extending therethrough, comprising:

a flexible, elongated tubular member having proximal and distal portions thereof and having an internal axially disposed lumen;

at least one traction element extending through said lumen and attached to said distal portion of said tubular member and having a proximal end projecting from said proximal portion of said tubular member, at least a portion of said traction element outside said tubular member for a distance along said tubular member, and manipulative handle attached to said proximal portion of said tubular member and to said proximal end of said traction element for exerting tension on said traction element at said proximal end to form the said tubular element to a desired degree of curvature depending upon the amount of tension and whereby said distal portion of said catheter or lead is similarly curved, wherein said manipulative handle comprises:

a longitudinal housing having a distal end thereof attached to said proximal end of said tubular element and receiving said proximal end of said traction element therewithin;

a reciprocating hinge lever coupled for pivotal motion with respect to said longitudinal housing and adapted to be disposed transversely therewithin;

means for attaching said proximal end of said traction element to said lever; and slide means coupled to said lever and adapted to slide upon said longitudinal housing for advancing and retracting a free end of said lever and thereby releasing and applying traction to said traction element to release or induce curvature in the distal portion of said elongated flexible tubular member.

6. A stylet and manipulative handle assembly for insertion into the proximal opening in the lumen of a hollow elongated catheter or lead body for imparting a curvature in a portion thereof and enabling the rotation thereof by manipulation of the handle at the proximal end of the elongated catheter or lead body, said stylet assembly comprising:

a two piece stylet adapted to be inserted into said proximal opening and through the length of said lumen, said stylet comprising;

an elongated hollow tubular member having proximal and distal ends and portions and at least one opening in the side thereof;

a length of pull wire extending within the tubular member through a proximal opening therein and through said side opening and extending outside the tubular member for a predetermined distance, a portion of said tubular member extending along said predetermined distance being compressed upon itself such that said tubular member is flattened only along the side of said side opening; and means for engaging the distal end of said pull wire with the distal end of said tubular member, so that traction applied proximally on said pull wire tends to induce a curvature in said tubular member; and manipulative handle means coupled to the proximal end of said tubular member and receiving said pull wire further comprising means for applying traction to said pull wire in said proximal direction to induce a curvature in said hollow tubular member.

7. The assembly of claim 6 wherein said tubular member further comprises:

a second side opening adjacent to the distal tip thereof and located said predetermined distance from said first opening and wherein:

said pull wire extending outside said distal portion of said tubular member is threaded into said second opening and;

said engaging means is adapted to mechanically couple the distal ends of said pull wire and said tubular member together.

8. The stylet assembly of claim 6 or claim 7 wherein said manipulative handle means further comprises:

an elongated tubular housing having a necked down portion with an axially disposed opening in said necked down portion for receiving said proximal end of said elongated tubular member and the proximal portion of said pull wire of said stylet therein;

a thumb actuable slidable member disposed around at least a portion of the length of said tubular housing;

moveable lever means having a predetermined length adapted to being pivotally coupled at one end to said housing and at the other end to said slidable member; and means for attaching said pull wire to said moveable lever for applying traction thereto upon proximal movement of said slidable member and said other end of said lever in relation to said housing.

* * * * *